United States Patent
Fukui et al.

(10) Patent No.: US 10,267,747 B2
(45) Date of Patent: Apr. 23, 2019

(54) SURFACE DEFECT INSPECTING DEVICE AND METHOD FOR STEEL SHEETS

(71) Applicant: NISSHIN STEEL CO., LTD., Tokyo (JP)

(72) Inventors: Keita Fukui, Tokyo (JP); Syunsuke Shiga, Tokyo (JP)

(73) Assignee: NISSHIN STEEL CO., LTD., Tokyo (JP)

( * ) Notice: Subject to any disclaimer, the term of this patent is extended or adjusted under 35 U.S.C. 154(b) by 0 days.

(21) Appl. No.: 16/123,141

(22) Filed: Sep. 6, 2018

(65) Prior Publication Data

US 2019/0003987 A1    Jan. 3, 2019

Related U.S. Application Data

(63) Continuation of application No. PCT/JP2016/074638, filed on Aug. 24, 2016.

(30) Foreign Application Priority Data

Mar. 30, 2016  (JP) ................................. 2016-067003

(51) Int. Cl.
*G01N 21/892* (2006.01)
*G01N 21/88* (2006.01)
(Continued)

(52) U.S. Cl.
CPC ..... *G01N 21/8921* (2013.01); *G01N 21/8851* (2013.01); *G01N 21/892* (2013.01);
(Continued)

(58) Field of Classification Search
CPC combination set(s) only.
See application file for complete search history.

(56) References Cited

U.S. PATENT DOCUMENTS

| 5,835,220 A | * | 11/1998 | Kazama | G01J 4/04 356/369 |
| 6,697,151 B2 | * | 2/2004 | Owen | B23K 3/08 356/237.1 |

(Continued)

FOREIGN PATENT DOCUMENTS

| CN | 103226108 A | 7/2013 |
| EP | 3279645 A1 | 2/2018 |

(Continued)

OTHER PUBLICATIONS

Japanese Office Action, dated Jan. 30, 2017, for Japanese Patent Application No. 2016-067003, with English Translation.
(Continued)

*Primary Examiner* — Anand P Bhatnagar
(74) *Attorney, Agent, or Firm* — Lynette Wylie; Apex Juris, PLLC.

(57) ABSTRACT

A surface defect inspecting device for steel sheets includes: an illuminating unit configured to illuminate an imaging target portion on a surface of a steel sheet; first and second diffuse reflection light imaging units arranged at a first angle and at a second angle larger than the first angle with respect to a specular reflection direction of illuminated light reflected from the imaging target portion, respectively, imaging simultaneously reflection light of illuminated light reflected from the imaging target portion; and an image signal processor configured to process first and second diffuse reflection image signals acquired by the first and second diffuse reflection light imaging units, respectively, detecting, as a surface defect portion, a portion for which brightness level is lower than a first predetermined threshold in the first diffuse reflection image signal as well as higher than a second predetermined threshold in the second diffuse reflection image signal.

4 Claims, 8 Drawing Sheets

(51) Int. Cl.
*G01N 21/89* (2006.01)
*G01N 33/2045* (2019.01)

(52) U.S. Cl.
CPC ..... *G01N 21/8914* (2013.01); *G01N 33/2045* (2019.01); *G01N 2021/8854* (2013.01); *G01N 2021/8887* (2013.01); *G01N 2021/8918* (2013.01)

(56) References Cited

U.S. PATENT DOCUMENTS

| | | | | |
|---|---|---|---|---|
| 7,248,366 | B2* | 7/2007 | Uesugi | B21C 51/005 356/237.2 |
| 10,041,888 | B2* | 8/2018 | Fukui | G01N 21/892 |
| 2002/0154295 | A1* | 10/2002 | Ivakhnenko | G01N 15/0211 356/237.2 |
| 2002/0154308 | A1 | 10/2002 | Uesugi et al. | |
| 2004/0207836 | A1* | 10/2004 | Chhibber | G01N 21/4738 356/237.4 |
| 2006/0181700 | A1* | 8/2006 | Andrews | G01N 21/21 356/237.2 |
| 2006/0186362 | A1* | 8/2006 | Bills | G01N 21/21 250/559.46 |
| 2006/0197945 | A1* | 9/2006 | Tiemeyer | G01N 21/21 356/237.2 |
| 2009/0091768 | A1* | 4/2009 | Itoh | G01M 11/00 356/611 |
| 2013/0215404 | A1* | 8/2013 | Den Boef | G01J 3/4412 355/44 |
| 2015/0168311 | A1* | 6/2015 | Seki | G01N 21/9501 356/51 |
| 2015/0192529 | A1* | 7/2015 | Sato | G01N 21/88 438/16 |

FOREIGN PATENT DOCUMENTS

| | | |
|---|---|---|
| JP | 11-295241 A | 10/1999 |
| JP | 2004-151006 A | 5/2004 |
| JP | 2006-242886 A | 9/2006 |
| JP | 2007-271510 A | 10/2007 |
| JP | 2010-249685 A | 11/2010 |
| JP | 5594071 B | 8/2014 |
| JP | 2015-200603 A | 11/2015 |
| KR | 10-2011-0119080 A | 11/2011 |
| KR | 10-2016-0027238 A | 3/2016 |

OTHER PUBLICATIONS

Korean Office Action, dated Dec. 15, 2017, for Korean Patent Application No. 10-2017-7034753, with English Translation.
Korean Decision of Refusal, dated Mar. 23, 2018, for Korean Patent Application No. 10-2017-7034753, with English Translation.
Chinese Office Action, dated Apr. 16, 2018, for Chinese Patent Application No. 201680014977.6, with English Translation.
Extended European Search Report dated Oct. 30, 2018, for European Patent Application No. 16896997.0.

* cited by examiner

| No. | Brightness level of reflection image signals ||| Aspect ratio | Types of abnormality in appearance |
|---|---|---|---|---|---|
| | First diffuse reflection image signals | Second diffuse reflection image signals ||| |
| | Density | | Density | | |
| 1 | dark | bright | b1<B | c1<C | scratch A |
| 2 | dark | bright | b2<B | c2<C | scratch B |
| 3 | dark | bright | b3<B<b3' | c3<C | scab |
| 4 | dark | dark | | | oil spot |
| 5 | dark | dark | | | annealing streak |

FIG. 6

SURFACE DEFECT INSPECTING DEVICE AND METHOD FOR STEEL SHEETS

CROSS REFERENCE TO RELATED APPLICATIONS

This is a continuation application of International Patent Application No. PCT/JP2016/074638 filed on Aug. 24, 2016 claiming priority upon Japanese Patent Application No. 2016-067003 filed on Mar. 30, 2016, of which full contents are incorporated herein by reference.

BACKGROUND OF THE INVENTION

Field of the Invention

The present invention relates to a surface defect inspecting device and a method for steel sheets.

Description of the Background Art

There have been abnormalities in appearance, such as scratch, scab, dirt, oil spot, annealing streak, generated on surfaces of steel sheets undergoing a cold rolling operation, annealing operation so as to be manufactured. The scratch, scab, dirt are harmful abnormalities in appearance i.e. surface defects, and for this reason, the steel sheets having such defects generated on the surfaces thereof have been regarded as being defective products. Meanwhile, the oil spot, annealing streak are harmless abnormalities in appearance, and therefore, the steel sheets having such abnormalities in appearance have not been regarded as being defective products. As a result, it has been requested that, in the manufacturing field of the steel sheets, harmful or harmless abnormalities in appearance be discriminated from each other with high precision.

Conventionally, there have been proposed surface inspecting devices for steel sheets each configured to: illuminate a surface of a steel sheet; image reflection light reflected from the surface to obtain image data; and analyze the image data thereby checking the presence or absence of surface defects. Such sorts of technique are disclosed in e.g. Patent Documents 1, 2.

Patent Document 1 discloses a dross defect inspecting device configured to classify the surface defects on hot-dip zinc-coated steel sheets as dross and other defects. The device is configured to illuminate a surface of a hot-dip zinc-coated steel sheet with light at an angle of 50-80° with respect to a normal line of the steel sheet, and image diffuse reflection light, through the use of a diffuse reflection camera, in a direction at an angle of 0-40° with respect to the normal line so as to acquire image signals. Out of the acquired signals, the device is further configured to classify a portion having brightness level lower than a predetermined threshold and area falling within a predetermined range as dross, and classify a portion having brightness level lower than a predetermined threshold and area falling outside a predetermined range as other surface defects.

A quality control device disclosed in Patent Document 2 is configured such that a combination of a specular reflection camera and a diffuse reflection camera is used. The quality control device is configured to, initially, illuminate a surface of a hot-dip zinc-coated steel sheet with light, and image specular reflection light as a reflected light of an illuminated light so as to acquire reflection image signals and perform extraction of image signals indicative of possible defects from acquired reflection image signals, and also image diffuse reflection light as a reflected light of the illuminated light so as to acquire reflection image signals and perform extraction of image signals indicative of possible defects from acquired reflection image signals. The extraction of the image signals indicative of possible defects is performed individually, for the specular reflection light and the diffuse reflection light, through the use of thresholds each set at a certain level of quality. The quality control device is configured to, subsequently, read basic information such as "linear flaw," "non-coating" set in advance, for each defect type, so as to select the image signals of true defects out of the image signals indicative of possible defects and acquire information about distribution of the image signals of true defects for each defect type. The quality control device is configured to, still subsequently, calculate a defect length, for each defect type, based upon acquired information, and determine, on the basis of a ratio of a calculated defect length relative to an entire length of the steel sheet and the like, whether a level of quality is achieved or not.

PRIOR ART DOCUMENTS

Patent Documents

Patent Document 1 Japanese Patent No. 5594071
Patent Document 2 Japanese Unexamined Patent Application Publication No. 2004-151006

Problem to be Solved

If an inspection target material is a coated steel sheet such as the inspection targets for the devices disclosed in Patent Documents 1, 2, the possible abnormalities in appearance generated on the surface are non-coating, pinhole non-coating, scab, dross, dirt, and the like. If the inspection target material is an uncoated steel sheet, however, the possible abnormalities in appearance generated on the surface are scratch, scab, oil spot, annealing streak, and the like. Out of such abnormalities in appearance, it is requested that harmful abnormalities in appearance e.g. surface defects such as scratch, scab, and harmless abnormalities in appearance such as oil spot, annealing streak be detected by the surface inspecting device so as to be discriminated from each other. It is to be noted that the scratch is defined as a defect generated on the steel sheet, when the steel sheet is rolled, in such a manner that different portions thereof rub against one another.

The device disclosed in Patent Document 1 is configured such that only one diffuse reflection camera is used. Such a configuration (mono optical system) having only one diffuse reflection camera provides dark image of scratch, scab, oil spot, annealing streak, which is low in brightness level, unless the threshold for the brightness level is set appropriately. For this reason, there cannot be discriminated between: scratch, scab, or the like as harmful abnormalities in appearance; and oil spot, annealing streak, or the like as harmless abnormalities in appearance.

The device disclosed in Patent Document 2 is configured such that a combination of a specular reflection camera and a diffuse reflection camera is used. Specular reflection light has characteristics of high detection sensitivity; however, it cannot provide stable inspection results for uncoated steel sheets, which is different from the case where coated steel sheets are the inspection targets, due to the fact that the uncoated steel sheets have the surfaces thereof applied with oil whose ununiformity causes the light reflected from the base texture to vary in brightness, which is problematic.

SUMMARY OF THE INVENTION

In view of the above-described problems, there is provided the present invention whose objective is to provide a surface defect inspecting device and method for steel sheets. More specifically, the present invention is provided as a surface defect inspecting device and method for steel sheets capable of detecting harmful abnormalities in appearance such as scratch, scab (surface defects) in a discriminatory manner from harmless abnormalities in appearance such as oil spot, annealing streak, on uncoated or untreated steel sheet surfaces.

Means for Solving Problems

A surface defect inspecting device for steel sheets, according to the present invention, includes: an illuminating unit configured to illuminate an imaging target portion on a surface of a steel sheet; a first diffuse reflection light imaging unit configured to image diffuse reflection light reflected from the imaging target portion in a direction of a first angle with respect to a specular reflection direction of illuminated light; a second diffuse reflection light imaging unit configured to image diffuse reflection light reflected from the imaging target portion in a direction of a second angle greater than the first angle with respect to a specular reflection direction of illuminated light; and an image signal processing unit configured to process a first diffuse reflection image signal acquired by the first diffuse reflection light imaging unit as a result of performing imaging and a second diffuse reflection image signal acquired by the second diffuse reflection light imaging unit as a result of performing imaging. The first diffuse reflection light imaging unit and the second diffuse reflection light imaging unit simultaneously image diffuse reflection light reflected from the imaging target portion. The image signal processing unit detects, as a surface defect portion, a portion for which brightness level is lower than a first predetermined threshold in the first diffuse reflection image signal acquired by the first diffuse reflection light imaging unit as a result of performing imaging as well as higher than a second predetermined threshold in the second diffuse reflection image signal acquired by the second diffuse reflection light imaging unit as a result of performing imaging.

According to the above-configured surface defect inspecting device for steel sheets, by e.g. setting the first predetermined threshold to be a value of the first diffuse reflection image signal acquired by the first diffuse reflection light imaging unit as a result of performing imaging of a base texture or to be a value close thereto, and setting the second predetermined threshold to be a value of the second diffuse reflection image signal acquired by the second diffuse reflection light imaging unit as a result of performing imaging of a base texture or to be a value close thereto, harmful abnormalities in appearance (surface defects) can be detected in a discriminatory manner from harmless abnormalities in appearance on uncoated or untreated surfaces of the steel sheets as inspection targets.

In the surface defect inspecting device for steel sheets configured above, it is preferable that the image signal processing unit sets the first predetermined threshold based upon a value of the first diffuse reflection image signal acquired by the first diffuse reflection light imaging unit as a result of performing imaging of a base texture, and sets the second predetermined threshold based upon a value of the second diffuse reflection image signal acquired by the second diffuse reflection light imaging unit as a result of performing imaging of a base texture.

In the surface defect inspecting device for steel sheets configured above, it is preferable that e.g. the first angle is within a range of 0-20°, and the second angle is within a range of 10-45°.

A surface defect inspecting method for steel sheets, according to the present invention, includes the steps of: illuminating an imaging target portion on a surface of a steel sheet; imaging diffuse reflection light reflected from the imaging target portion at a first angle with respect to a specular reflection direction of illuminated light, and diffuse reflection light reflected from the imaging target portion at a second angle greater than the first angle with respect to a specular reflection direction of illuminated light, respectively; and processing a first diffuse reflection image signal acquired as a result of performing imaging and a second diffuse reflection image signal acquired as a result of performing imaging, respectively. The diffuse reflection light reflected from the imaging target portion in a direction of the first angle, and the diffuse reflection light reflected from the imaging target portion in a direction of the second angle are simultaneously imaged. In a step of said processing, a portion, for which brightness level is lower than a first predetermined threshold in the first diffuse reflection image signal acquired as a result of performing imaging as well as higher than a second predetermined threshold in the second diffuse reflection image signal acquired as a result of performing imaging, is detected as a surface defect portion.

According to the above-configured surface defect inspection method for steel sheets, by e.g. setting the first predetermined threshold to be a value of the first diffuse reflection image signal acquired as a result of performing imaging of a base texture or to be a value close thereto, and setting the second predetermined threshold to be a value of the second diffuse reflection image signal acquired as a result of performing imaging of a base texture or to be a value close thereto, harmful abnormalities in appearance (surface defects) can be detected in a discriminatory manner from harmless abnormalities in appearance on uncoated or untreated surfaces of the steel sheets as inspection targets.

In the surface defect inspecting method for steel sheets configured above, it is preferable that the first predetermined threshold is set based upon a value of the first diffuse reflection image signal acquired as a result of performing imaging of a base texture, and the second predetermined threshold is set based upon a value of the second diffuse reflection image signal acquired as a result of performing imaging of a base texture.

In the surface defect inspecting method for steel sheets configured above, it is preferable that e.g. the first angle is within a range of 0-20°, and the second angle is within a range of 10-45°

Advantageous Effects of the Invention

According to the present invention, harmful abnormalities in appearance (surface defects) can be detected in a discriminatory manner from harmless abnormalities in appearance on uncoated or untreated surfaces of the steel sheets as inspection targets.

BRIEF DESCRIPTIONS OF THE DRAWINGS

For more thorough understanding of the present invention and advantages thereof, the following descriptions should be read in conjunction with the accompanying drawings in which:

FIG. 6 depicts a correspondence table showing an example of conditions for determining types of abnormality in appearance.

DESCRIPTIONS OF EMBODIMENTS OF THE INVENTION

Hereafter, a surface defect inspecting device and method for steel sheets as an embodiment of the present invention will be described with reference to the drawings. Steel sheets in an embodiment are uncoated or untreated steel sheets having the surfaces thereof applied with oil.

Figure 1:
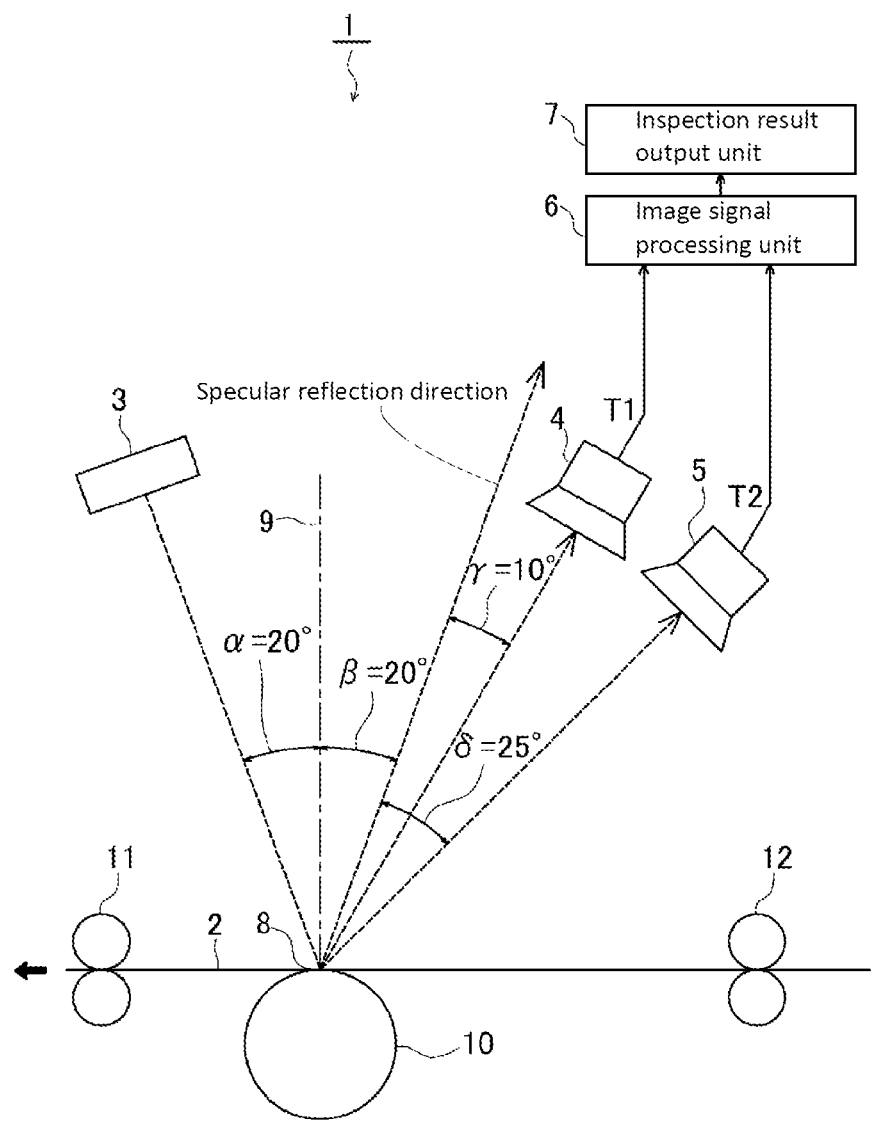
FIG. 1 depicts a structurally exemplified view of a surface defect inspecting device for steel sheets.

As shown in FIG. 1, a surface defect inspecting device (1) in an embodiment detects harmful abnormalities in appearance such as scratch, scab in a discriminatory manner from harmless abnormalities in appearance such as oil spot, annealing streak on a surface of a steel sheet (2). The surface defect inspecting device (1) includes an illuminating unit (3), a first diffuse reflection light imaging unit (4), a second diffuse reflection light imaging unit (5), an image signal processing unit (6), an inspection result output unit (7), and the like. It is preferable that a surface defect inspection of the steel sheet (2) is made by the surface defect inspecting device (1) under the circumstances where the steel sheet (2) is positioned so as not to fluctuate in a thickness direction thereof. In an example shown in FIG. 1, the steel sheet (2) is pinched by pinch rollers (11, 12) at both sides thereof, and a position at which the steel sheet (2) is supported by a roller (10) between both the sides thereof is a position for inspection where the steel sheet (2) is not caused to fluctuate in a thickness direction thereof (an imaging target portion (8) that will be described later).

The illuminating unit (3) illuminates an imaging target portion (8) on a surface of the steel sheet (2). The illuminating unit (3) is arranged on a downstream side, along a conveyance direction of the steel sheet (2), with respect to a plane (9) defined virtually as being orthogonal to a conveyance direction of the steel sheet (2) at the imaging target portion (8) (hereafter, occasionally referred to as "orthogonal plane (9)") in such a manner that light is incident on the surface of the steel sheet (2) at a predetermined incidence angle of α (α=20° in an embodiment) with respect to the orthogonal plane (9). In an embodiment, as a light source of the illuminating unit (3), an LED line illuminator configured to illuminate the steel sheet (2) in a plate width direction is adopted. The light source of the illuminating unit (3) is not so limitative, however, and halogen, metal halide fluorescent lamps, other than an LED, may be adopted alternatively.

The first diffuse reflection light imaging unit (4) images diffuse reflection light reflected from the imaging target portion (8) on the surface of the steel sheet (2) illuminated with light by the illuminating unit (3). The first diffuse reflection light imaging unit (4) is arranged on an upstream side, along a conveyance direction of the steel sheet (2), with respect to the orthogonal plane (9) in such a manner that the first diffuse reflection light imaging unit (4) receives the diffuse reflection light at a first angle of γ (γ=10° in an embodiment) with respect to a specular reflection direction of the reflected illuminating light (the specular reflection direction forms an angle of β (β=20°) with respect to the orthogonal plane (9) in an embodiment). In an embodiment, the first diffuse reflection light imaging unit (4) adopts a CCD line sensor camera. It may be replaced by e.g. a CCD area sensor camera. It is to be noted that a spatial resolution for detection by the first diffuse reflection light imaging unit (4) is set appropriately in accordance with defect types of surface defects as detection targets.

The second diffuse reflection light imaging unit (5) images diffuse reflection light reflected from the imaging target portion (8) on the surface of the steel sheet (2) illuminated with light by the illuminating unit (3). The second diffuse reflection light imaging unit (5) is arranged on an upstream side, along a conveyance direction of the steel sheet (2), with respect to the orthogonal plane (9) in such a manner that the second diffuse reflection light imaging unit (5) receives the diffuse reflection light reflected at a second angle of δ (δ=25° in an embodiment) with respect to the specular reflection direction of the reflected illuminating light. The second diffuse reflection light imaging unit (5) may adopt a similar type to the first diffuse reflection light imaging unit (4).

The image signal processing unit (6) processes first diffuse reflection signals T1 acquired by the first diffuse reflection light imaging unit (4) as a result of performing imaging and second diffuse reflection signals T2 acquired by the second diffuse reflection light imaging unit (5) as a result of performing imaging, so as to extract surface defects on the steel sheet (2) and determine defect types by classifying the extracted surface defects. The image signal processing unit (6) includes various arithmetic processors (e.g. a personal computer, PC, installed with a program necessary to carry out classification-determination logic that will be described later).

The inspection result output unit (7), upon extraction of the surface defects by the image signal processing unit (6), transmits the detection of the surface defects and the types of the detected surface defects to a present manufacturing process, a subsequent manufacturing process, or users by means of e.g. displaying or printing. The inspection result output unit (7) includes e.g. a monitor, printer, and the like.

It is to be noted that, although a place for arranging the surface defect inspecting device (1) is not particularly limitative, it is preferred that the surface defect inspecting device (1) be arranged in a place where a step of inspecting the surface defects is completed immediately before a step of winding steel sheets (2) around a tension reel.

Figure 2:
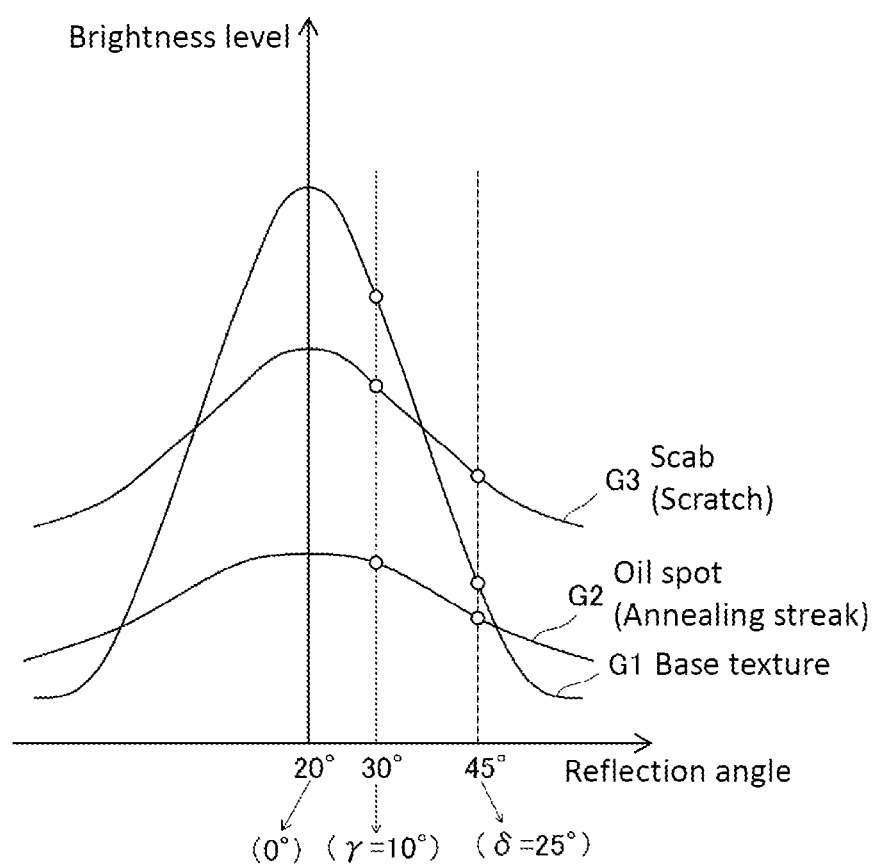
FIG. 2 depicts a graph showing a relation of brightness levels of reflection light as a function of reflection angles with respect to a base texture, scab, scratch, oil spot, annealing streak.

The relation between reflection angles and brightness levels of light reflected from the surface of the steel sheet (2) is qualitatively different for each of base texture and types of abnormality in appearance. It is preferred that, in view of the above, a light receiving angle γ of the first diffuse reflection light imaging unit (4) and a light receiving angle δ of the second diffuse reflection light imaging unit (5) be set individually. The graph illustrated in FIG. 2 shows the above-described relation in a horizontal axis representing reflection angles with respect to the orthogonal plane (9) (the angles in parentheses indicate angles with respect to the specular reflection direction), and a vertical axis representing brightness levels. The curve G1 shows a relation for a light-reflection surface with a base texture; the curve G2 shows a relation for a light-reflection surface with oil spot or annealing streak (hereafter, represented by "oil spot" only); and the curve G3 shows a relation for a light-reflection surface with scab or scratch (hereafter, represented by "scab" only). The curves G1-G3 all show that each brightness level is the maximum at an angle, which is a specular reflection angle with respect to the orthogonal plane (9), of 20°, and that, with increase in each reflection angle from a specular reflection angle of 20°, the brightness level decreases. Such decrease in brightness level is much more significant for the base texture in comparison with abnormalities in appearance i.e. the oil spot, scab, and the like. The brightness level of the reflection light is higher for the scab in comparison with the oil spot over an entire range of reflection angles.

In an embodiment, the first diffuse reflection light imaging unit (4) is arranged at a reflection-angle position (a position at which γ is equal to 10° in an embodiment) where a brightness level for a light-reflection surface with the scab (curve G3) is lower than a brightness level for a light-reflection surface with the base texture as a reference level (curve G1) (or a brightness level lower than the reference level by a predetermined value), and a brightness level for a light-reflection surface with the oil spot (curve G2) is also lower than the reference level (curve G1) (or a brightness level lower than the reference level by a predetermined value). Meanwhile, the second diffuse reflection light imaging unit (5) is arranged at a reflection-angle position (a position at which δ is equal to 25° in an embodiment) where a brightness level for a light-reflection surface with the scab (curve G3) is higher than the reference level (curve G1), and a brightness level for a light-reflection surface with the oil spot (curve G2) is lower than the reference level (curve G1).

Figure 3:
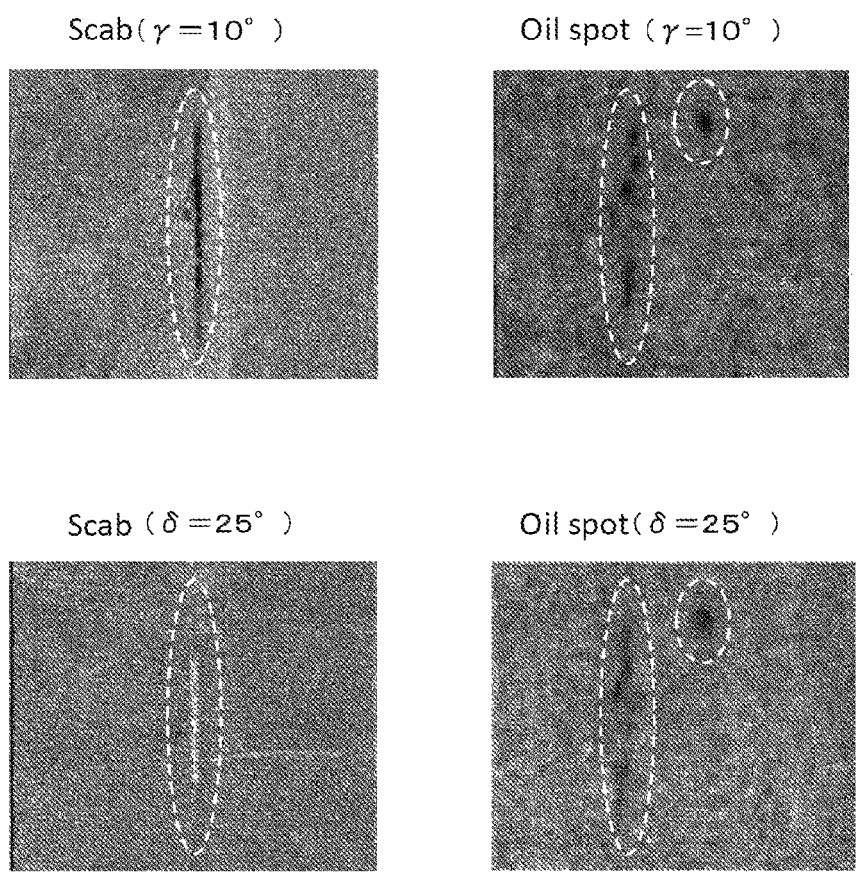
FIG. 3 depicts a variety of pieces of image view of scab, oil spot generated on a surface of a steel sheet.

The abnormality in appearance looking black or white enclosed with white dashed line in each piece of image shown in FIG. 3 is related to the scab and oil spot generated on the surface of the steel sheet (2). As shown in FIG. 3, "Scab (γ=10°)" and "Oil spot (γ=10°)" each represents image formed on the basis of the first diffuse reflection image signals acquired by the first diffuse reflection light imaging unit (4), and "Scab (δ=25°)" and "Oil spot (δ=25°)" each represents image formed on the basis of the second diffuse reflection image signals acquired by the second diffuse reflection light imaging unit (5).

As shown in "Scab (γ=10°)" and "Oil spot (γ=10°)" in FIG. 3, both the scab portion and the oil spot portion, in the case of an angle of 10° with respect to the specular reflection direction, look black (dark) in comparison with the surrounding base texture. Meanwhile, as shown in "Scab (δ=25°)" and "Oil spot (δ=25°)" in FIG. 3, the scab portion, in the case of an angle of 25° with respect to the specular reflection direction, looks white (bright) in comparison with the surrounding base texture, whereas the oil spot portion, in the case of an angle of 25° with respect to the specular reflection direction, looks black (dark) in comparison with the surrounding base texture, which are capable of being discriminated from each other.

Figure 4:
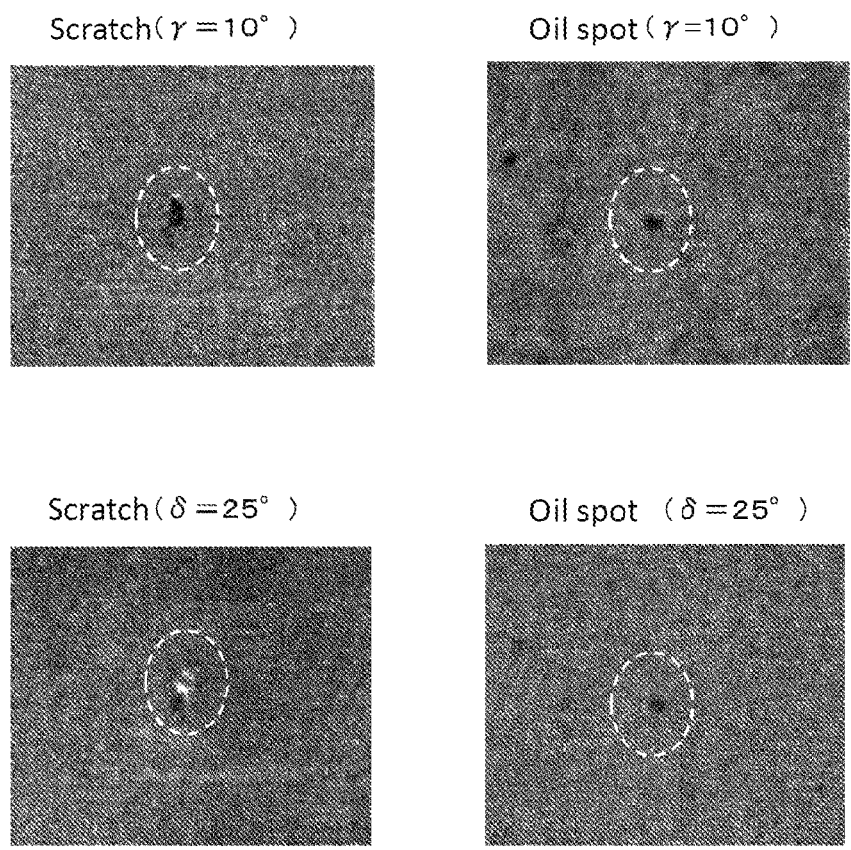
FIG. 4 depicts a variety of pieces of image view of scratch, oil spot generated on a surface of a steel sheet.

Furthermore, the abnormality in appearance looking black or white enclosed with white dashed line in each piece of image shown in FIG. 4 is related to the scratch and oil spot generated on the surface of the steel sheet (2). As shown in FIG. 4, "Scratch (γ=10°)" and "Oil spot (γ=10°)" each represents image formed on the basis of the first diffuse reflection image signals acquired by the first diffuse reflection light imaging unit (4), and "Scratch (δ=25°)" and "Oil spot (δ=25°)" each represents image formed on the basis of the second diffuse reflection image signals acquired by the second diffuse reflection light imaging unit (5).

As shown in "Scratch (γ=10°)" and "Oil spot (γ=10°)" in FIG. 4, both the scratch portion and the oil spot portion, in the case of an angle of 10° with respect to the specular reflection direction, look black (dark) in comparison with the surrounding base texture. Meanwhile, as shown in "Scratch (δ=25°)" and "Oil spot (δ=25°)" in FIG. 4, the scratch portion, in the case of an angle of 25° with respect to the specular reflection direction, looks white (bright) in comparison with the surrounding base texture, whereas the oil spot portion, in the case of an angle of 25° with respect to the specular reflection direction, looks black (dark) in comparison with the surrounding base texture, which are capable of being discriminated from each other.

As shown in FIG. 2, therefore, surface defects such as scab, scratch can be discriminated from harmless abnormalities in appearance such as oil spot, annealing streak by arranging the first diffuse reflection light imaging unit (4) at a reflection-angle position where a brightness level for a light-reflection surface with the scab (curve G3) is lower than a brightness level for a light-reflection surface with the base texture as a reference level (curve G1) (or a brightness level lower than the reference level by a predetermined value), and a brightness level for a light-reflection surface with the oil spot (curve G2) is also lower than the reference level (curve G1) (or a brightness level lower than the reference level by a predetermined value), and further, by arranging the second diffuse reflection light imaging unit (5) at a reflection-angle position where a brightness level for a light-reflection surface with the scab (curve G3) is higher than the reference level (curve G1), and a brightness level for a light-reflection surface with the oil spot (curve G2) is lower than the reference level (curve G1), and still further, by setting the reference level (curve G1) to be a threshold for the above discrimination.

Figure 5:
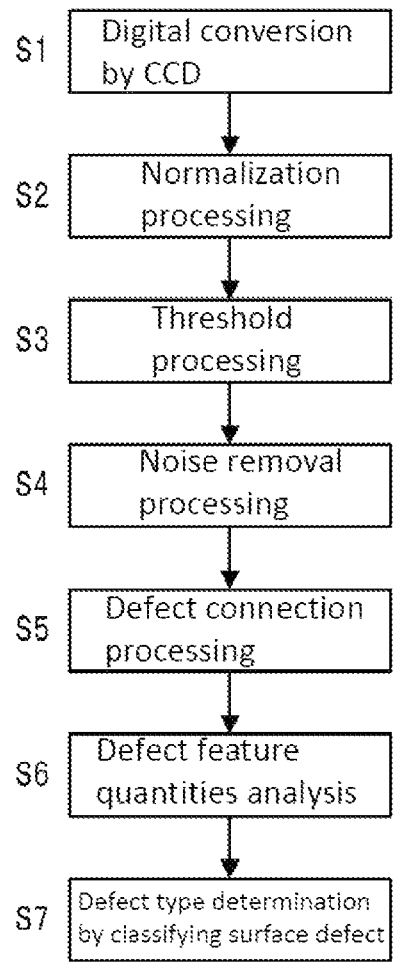
FIG. 5 depicts a flowchart showing steps from detecting defects on a surface through image signals acquired by imaging reflection light until determining defect types by classifying detected defects on the surface.

Hereafter, steps from imaging diffuse reflection light by each diffuse reflection light imaging units (4, 5) until detecting surface defects based upon acquired image signals and classifying detected surface defects will be explained with reference to FIG. 5.

Initially, the first diffuse reflection light imaging unit (4) and the second diffuse reflection light imaging unit (5) image the diffuse reflection lights reflected from the surface of the steel sheet (2), and perform digital conversion through the use of CCD to acquire first diffuse reflection image signals T1 and second diffuse reflection image signals T2 valued in 256 gradations, respectively (S1).

Figure 7:
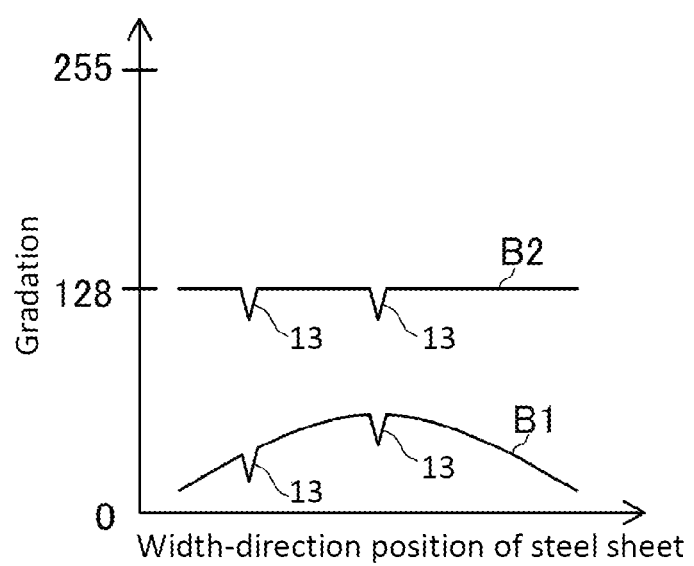
FIG. 7 depicts an explanatory view of normalization processing.

Subsequently, the image signal processing unit (6) performs normalization processing of the first diffuse reflection image signals T1 and the second diffuse reflection image signals T2 (S2), and thereafter performs threshold processing (S3) of them. The normalization processing is performed to correct variation and bias in the values of the image signals T1 and T2 mainly due to the aberration of the lenses of the imaging units (4, 5) as well as different illumination conditions in different imaging positions on the steel sheet (2). As the above-described normalization processing, the normal distribution e.g. $N(\mu, \sigma^2)$ with respect to the image signals T1 and T2 acquired in S1 is converted to the standard normal distribution $N(0, 1^2)$, where mean $\mu$ is equal to 0 and standard deviation $\sigma$ is equal to 1, and the mean is further adjusted from 0 to 128 in an offset manner. For instance, as shown in FIG. 7, when the values of the image signals T1 and T2 make a waveform centered along a curve B1 in a shape of gradual increase toward a center from both sides in a width direction of the steel sheet (2) before the normalization processing is performed, the values of the image signals T1 and T2 make a waveform centered along a line B2 without variation with a mean of 128 after the normalization processing is completed. In It is to be noted that, as shown in FIG. 7, the vertical axis represents gradation from 0 to 255 and the horizontal axis represents positions in a width direction of the steel sheet (2), and the ends of the curve B1 and the line B2 correspond to the ends of the steel sheet (2), and the projections (13) protruding downward from the curve B1 and the line B2 indicate image signals indicative of abnormalities in appearance.

In the threshold processing of the first diffuse reflection image signals T1, the first diffuse reflection image signals T1L having brightness level lower than a predetermined threshold P1 are extracted as corresponding to an abnormal-in-appearance portion. The above-described threshold P1 is set to be a value based upon a value of the first diffuse reflection image signals T1 acquired by the first diffuse reflection light imaging unit (4) as a result of imaging the first diffuse reflection light from the base texture. In an embodiment, the above-described threshold P1 is set to be a value lower, by a predetermined value, than a shift average value of the first diffuse reflection image signals T1 in the imaging range of the first diffuse reflection light imaging unit (4).

In the threshold processing of the second diffuse reflection image signals T2, for the above-described abnormal-in-appearance portion (a portion on the steel sheet (2) with the first diffuse reflection image signals T1 having brightness level lower than the predetermined threshold P1), a portion for which brightness level of the second diffuse reflection image signals T2H is higher than a predetermined threshold P2 is classified as a surface defect portion (scab or scratch), and a portion for which brightness level of the second diffuse reflection image signals T2L is lower than the predetermined threshold P2 is classified as a harmless abnormal-in-appearance portion (oil spot or annealing streak in an embodiment). The above-described threshold P2 is set to be a value based upon a value of the second diffuse reflection image signals T2 acquired by the second diffuse reflection light imaging unit (5) as a result of imaging the second diffuse reflection light from the base texture. In an embodiment, the above-described threshold P2 is set to be a shift average value of the second diffuse reflection image signals T2 in the imaging range of the second diffuse reflection light imaging unit (5).

Figure 8:
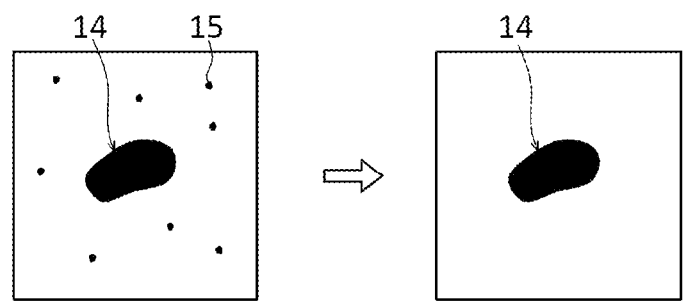
FIG. 8 depicts an explanatory view of noise removal processing.
Figure 9:
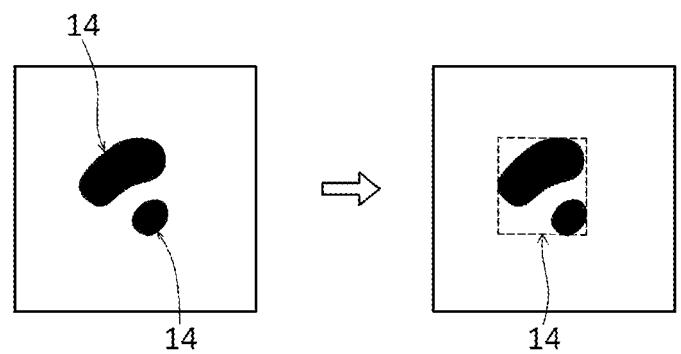
FIG. 9 depicts an explanatory view of defect connection processing.

Still subsequently, the image signal processing unit (6) performs noise removal processing (S4) to extract pixels regarded as being surface defect portions in the threshold processing of the second diffuse reflection image signals T2, and thereafter performs defect connection processing (S5) of the extracted pixels of surface defect portions so as to connect thereamong. In the noise removal processing, out of defect pixels (14, 15) detected in the above-described threshold processing, defect pixels (15) in the form of isolated points (minute defects) capable of being discriminated from their neighborhood are regarded as being noises as shown in a left-sided view of FIG. 8, and are changed to normal pixels as shown in right-sided view of FIG. 8. A filter for changing the defect pixels (14) to normal pixels (means for noise removal processing) has been well-known as averaging filter, low-pass filter, Gaussian filter, Laplacian filter, and so forth. In the defect connection processing, e.g., defects (14) adjacent to one another, as shown in a left-sided view of FIG. 9, located in one area (exemplified by a square area surrounded by dashed lines in a right-sided view of FIG. 9) are recognized as being a single defect (14).

Based upon a contour of the surface defect portion recognized as the single defect (14) in the defect connection processing, the image signal processing unit (6) analyzes the feature quantities of the surface defect portion such as aspect ratio. Furthermore, the image signal processing unit (6) calculates a ratio in density between: pixels regarded as surface defect portions in the threshold processing for the second diffuse reflection image signals T2; and pixels within the area defined by the contour (S6).

Finally, the image signal processing unit (6) applies threshold conditions on aspect ratio, density, and the like set for each surface defect type as shown in FIG. 6, to the surface defect portions, so as to classify their types (scratch, scab) (S7). In an embodiment, the extracted surface defects are classified into: "scratch A"; "scratch B"; and "scab." In the threshold conditions shown in FIG. 6, the capital letters "A," "B," and "C" represent the actual values obtained in surface defect inspections, and the small letters followed by numbers "a1," "b1," "c1," . . . represent predetermined threshold values. Such threshold values are optimal values obtained by repeating experiments and studies on respective types of surface defects. "Dark" in the column of "First diffuse reflection image signals" denotes brightness lower than the above-described threshold P1. "Dark" in the column of "Second diffuse reflection image signals" denotes brightness level lower than the above-described threshold P2, and "bright" in the column of "Second diffuse reflection image signals" denotes brightness level higher than the above-described threshold P2.

As clarified from the above descriptions, by virtue of the surface defect inspecting device and method for steel sheets as an embodiment according to the present invention, the simultaneous and combined use of pieces of information about brightness of the diffuse reflection image signals obtained from the diffuse reflection light reflected in two directions enables detection of harmful abnormalities in appearance (surface defects such as scratch, scab) in a discriminatory manner from harmless abnormalities in appearance such as oil spot, annealing streak.

Further, by virtue of the surface defect inspecting device and method for steel sheets as an embodiment according to the present invention, there is not used specular reflection light but used only diffuse reflection light, and therefore, stable inspection results, without being influenced by the ununiformity of oil applied to the surface of the steel sheets, can be obtained.

Still further, by virtue of the surface defect inspecting device and method for steel sheets as an embodiment according to the present invention, the detected surface defects can be classified into scratch and scab.

In the above-described embodiments, angles for the optical system is set to be $\alpha=20°$, $\gamma=10°$, and $\delta=25°$. The angle $\alpha$ may be changed within a range of 10-25°. The angle $\gamma$ may be changed within a range of 0-20° on the premise that there is a relation of G1>G3>G2 in FIG. 2. The angle $\delta$ may be changed within a range of 10-45° on the premise that there is a relation of G3>G1>G2 in FIG. 2 as well as $\delta>\gamma$. The inventor has confirmed that the angles $\alpha$, $\gamma$, and $\delta$ set within their respective ranges described above ensure stable diffuse reflection signals T1 and T2 and, as a result, stable inspection results.

INDUSTRIAL APPLICABILITY

The present invention can be applied to e.g. a surface defect inspecting device and a method for cold-rolled steel sheets.

REFERENCE NUMERALS

1 Surface defect inspecting device
2 Steel sheet
3 Illuminating unit
4 First diffuse reflection light imaging unit
5 Second diffuse reflection light imaging unit
6 Image signal processing unit
7 Inspection result output unit
8 Imaging target portion
T1 First diffuse reflection image signals
T2 Second diffuse reflection image signals

What is claimed is:

1. A surface defect inspecting device for steel sheets, comprising:
    an illuminating unit having a light source configured to illuminate an imaging target portion, with light of the light source, on a surface of a steel sheet;
    a first diffuse reflection light imaging unit having a first light receiver arranged, at a first angle with respect to a specular reflection direction of illuminated light, in such a manner that the first diffuse reflection light imaging unit images reflection light, received by the first light receiver, reflected in a direction of the first angle from the imaging target portion so as not to image specular reflection light but to image first diffuse reflection light;
    a second diffuse reflection light imaging unit having a second light receiver arranged, at a second angle larger than the first angle with respect to a specular reflection direction of illuminated light, in such a manner that the second diffuse reflection light imaging unit images reflection light, received by the second light receiver, reflected in a direction of the second angle from the imaging target portion so as not to image specular reflection light but to image second diffuse reflection light; and
    an image signal processor configured to process a first diffuse reflection image signal acquired by the first diffuse reflection light imaging unit as a result of performing imaging and a second diffuse reflection image signal acquired by the second diffuse reflection light imaging unit as a result of performing imaging, wherein
    the first diffuse reflection light imaging unit and the second diffuse reflection light imaging unit simultaneously image reflection light reflected from the imaging target portion, and wherein
    the image signal processor detects, as a surface defect portion, a portion for which brightness level is lower than a first predetermined threshold in the first diffuse reflection image signal acquired by the first diffuse reflection light imaging unit as a result of performing imaging as well as higher than a second predetermined threshold in the second diffuse reflection image signal acquired by the second diffuse reflection light imaging unit as a result of performing imaging.

2. The surface defect inspecting device for steel sheets according to claim 1, wherein
    the image signal processor
    sets the first predetermined threshold based upon a value of the first diffuse reflection image signal acquired by the first diffuse reflection light imaging unit as a result of performing imaging of a base texture, and
    sets the second predetermined threshold based upon a value of the second diffuse reflection image signal acquired by the second diffuse reflection light imaging unit as a result of performing imaging of a base texture.

3. A surface defect inspecting method for steel sheets, comprising the steps of:
    illuminating, by an illuminating unit having a light source, an imaging target portion on a surface of a steel sheet;
    imaging, by a first diffuse reflection imaging unit having a first light receiver and a second diffuse reflection imaging unit having a second light receiver, a first diffuse reflection light reflected from the imaging target portion at a first angle with respect to a specular reflection direction of illuminated light and a second diffuse reflection light reflected from the imaging target portion at a second angle greater than the first angle with respect to a specular reflection direction of illuminated light, respectively, without imaging any specular reflection light reflected from the imaging target portion, and
    processing, by an image signal processor, a first diffuse reflection image signal acquired as a result of performing imaging and a second diffuse reflection image signal acquired as a result of performing imaging, respectively, wherein
    in a step of said imaging by the first diffuse reflection imaging unit and the second diffuse reflection imaging unit, the first diffuse reflection light and the second diffuse reflection light are simultaneously imaged, and wherein
    in a step of said processing by the image signal processor, a portion, for which brightness level is lower than a first predetermined threshold in the first diffuse reflection image signal acquired as a result of performing imaging as well as higher than a second predetermined threshold in the second diffuse reflection image signal acquired as a result of performing imaging, is detected as a surface defect portion.

4. The surface defect inspecting method for steel sheets according to claim 3, wherein
    the first predetermined threshold is set based upon a value of the first diffuse reflection image signal acquired as a result of performing imaging of a base texture, and
    the second predetermined threshold is set based upon a value of the second diffuse reflection image signal acquired as a result of performing imaging of a base texture.

* * * * *